(12) United States Patent
Siess et al.

(10) Patent No.: US 10,808,704 B2
(45) Date of Patent: Oct. 20, 2020

(54) BLOOD PUMP WITH MICROMOTOR

(75) Inventors: Thorsten Siess, Wuerselen (DE);
Frank Kirchhoff, Ubach-Palenberg (DE)

(73) Assignee: ABIOMED EUROPE GMBH, Aachen (DE)

( * ) Notice: Subject to any disclaimer, the term of this patent is extended or adjusted under 35 U.S.C. 154(b) by 1119 days.

(21) Appl. No.: 12/532,816

(22) PCT Filed: Mar. 14, 2008

(86) PCT No.: PCT/EP2008/053096
§ 371 (c)(1),
(2), (4) Date: Sep. 23, 2009

(87) PCT Pub. No.: WO2008/116765
PCT Pub. Date: Oct. 2, 2008

(65) Prior Publication Data
US 2010/0041939 A1    Feb. 18, 2010

(30) Foreign Application Priority Data

Mar. 24, 2007   (DE) ........................ 10 2007 014 224

(51) Int. Cl.
*A61M 1/00*        (2006.01)
*F04D 13/06*       (2006.01)
(Continued)

(52) U.S. Cl.
CPC ............ *F04D 13/064* (2013.01); *F04D 3/00* (2013.01); *F04D 13/0626* (2013.01);
(Continued)

(58) Field of Classification Search
CPC ....... A61M 1/101; A61M 1/122; A61M 1/125
(Continued)

(56) References Cited

U.S. PATENT DOCUMENTS 4,851,002 A * 7/1989 Slonina ............... A61M 1/1096
                                                    623/3.21
4,957,504 A * 9/1990 Chardack .................. 623/3.14
(Continued)

FOREIGN PATENT DOCUMENTS

DE         10005432       8/2000
JP         H06261508 A    9/1994
(Continued)

OTHER PUBLICATIONS

International Search Report and Written Opinion for Application No. PCT/EP2008/053096 dated Nov. 11, 2008.

*Primary Examiner* — Michael J D Abreu
(74) *Attorney, Agent, or Firm* — Botos Churchill IP Law LLP

(57) ABSTRACT

The invention relates to a micromotor (10), the stator of which contains a back iron jacket (18). Said back iron jacket consists of a continuous unslotted sleeve consisting of a metal alloy that contains ferritic iron as the main constituent, up to 30% chromium and preferably aluminium and yttrium oxide. Electric conductivity is reduced by the oxidation of the aluminium. The yttrium oxide performs the same function. The reduced electric conductivity suppresses eddy currents to a great extent. The back iron jacket (18) has a high magnetic conductivity with a small wall thickness, thus increasing the electrical output for a motor with a small diameter.

13 Claims, 2 Drawing Sheets

(51) Int. Cl.
*F04D 3/00* (2006.01)
*A61M 1/10* (2006.01)
*A61M 1/12* (2006.01)

(52) U.S. Cl.
CPC ........... *A61M 1/101* (2013.01); *A61M 1/1013* (2014.02); *A61M 1/1031* (2014.02); *A61M 1/1082* (2014.02); *A61M 1/1084* (2014.02); *A61M 1/122* (2014.02); *A61M 1/125* (2014.02)

(58) Field of Classification Search
USPC ................................................ 600/16; 604/9
See application file for complete search history.

(56) References Cited

U.S. PATENT DOCUMENTS

| | | | |
|---|---|---|---|
| 5,302,874 A | 4/1994 | Pinkerton | |
| 6,368,083 B1* | 4/2002 | Wampler | .................... 417/423.7 |
| 2003/0187321 A1* | 10/2003 | Hoffmann | ................. F04D 3/00 600/16 |
| 2006/0155158 A1* | 7/2006 | Aboul-Hosn | ......... A61M 1/101 600/16 |

FOREIGN PATENT DOCUMENTS

| | | |
|---|---|---|
| JP | H08206192 A | 8/1996 |
| JP | 9046951 | 2/1997 |
| JP | 9131016 | 5/1997 |
| JP | 2000511759 A | 9/2000 |
| JP | 2002-101619 A | 4/2002 |
| JP | 3607098 B2 | 1/2005 |
| JP | 2005-103266 A | 4/2005 |
| JP | 5753104 B2 | 7/2015 |
| WO | 0241935 | 3/2002 |

* cited by examiner

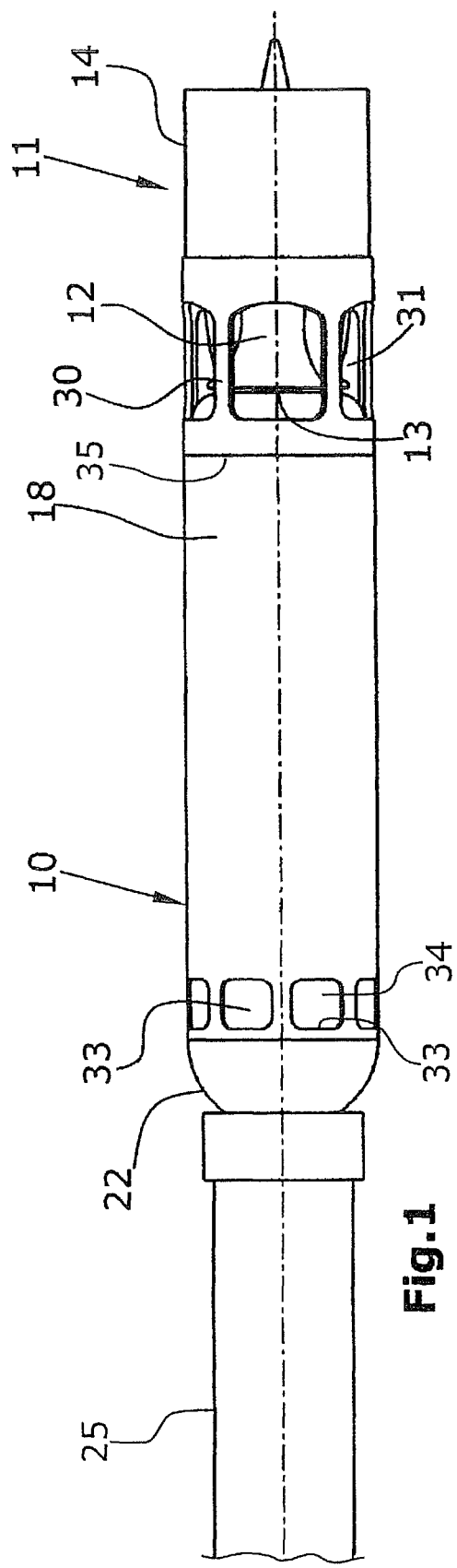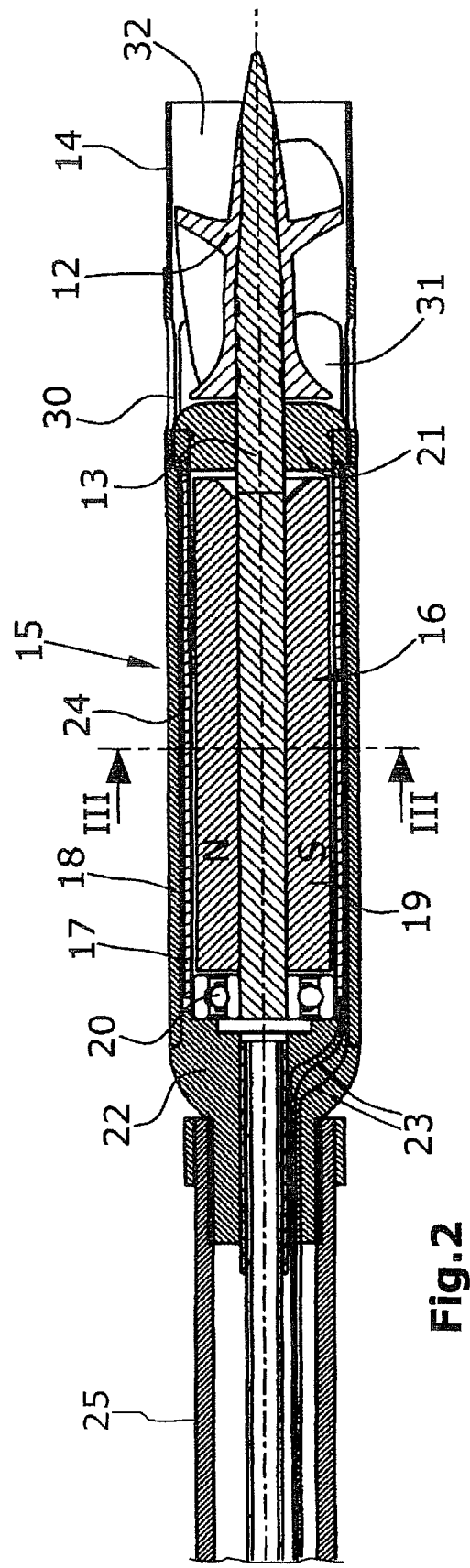
Fig.1
Fig.2

BLOOD PUMP WITH MICROMOTOR

RELATED APPLICATIONS

This application is a U.S. national phase of PCT/EP2008/053096, filed Mar. 14, 2008, which claims priority from Germany Application Serial No. 102007014224.4, filed Mar. 24, 2007.

The invention relates to a blood pump with micromotor, provided for intracorporeal use, and particularly a blood pump to be inserted intravascularly via a vascular sluice.

In the field of medical technology, a need exists for blood pumps which are inserted into the body of a patient and placed in a blood vessel (vein) or in the heart for supporting the cardiac function. A blood pump of this type for intravascular insertion has an outer diameter of 4-8 mm and a rigid length of less than 35 mm. For allowing such a small-sized blood pump to achieve the required physiological conveying capacity, a high rotational speed of the pump in the order of magnitude of 30,000-60,000 rpm is required.

WO 02/41935 A1 describes a blood pump with micromotor which meets the above outlined demands. The micromotor has an elongate tubular housing which also forms the stator. Said housing consists of a tubular shell containing an exciter coil, and a magnetic-reflux jacket of magnetically soft material surrounding said shell. The rotor comprises magnets arranged on a shaft. Said magnetic-reflux jacket serves for concentrating the magnetic fields generated by the magnets and for providing low-loss reflux paths for the magnetic flux. Thereby, the dissipation losses are kept small.

In said known micromotor, the magnetic-reflux jacket consists of an integral body assembled of parallel rings which are separated from each other by slots. Mutually adjacent rings are connected to each other by at least one bridge. The segmented configuration of the magnetic-reflux jacket serves for limiting eddy currents. Since the magnetic-reflux jacket has only a very small wall thickness of 0.2-0.4 mm, the cross-sectional area available for the magnetic flux is very narrow. As a result, the reflux is performed in state of magnetic saturation. As a consequence of the discontinuous configuration of the magnetic-reflux jacket due to the numerous slots, the effect of the magnetic-reflux jacket on the magnetic field is deteriorated, with a resultant increase of the magnetic losses caused by the escaping stray fields. This leads to an increase of the required motor current and, depending on the given case, to a larger motor volume.

It is an object of the invention to provide a blood pump with micromotor, of the type for intracorporeal use, wherein said pump has an increased power density so that the dimensions of the motor can be kept as small as possible.

The blood pump with micromotor as provided by the invention is defined by claim 1. Said blood pump comprises a magnetic-reflux jacket consisting of a one-pieced unslotted shell made of a material which is a ferritic iron alloy including up to 30% chromium.

The invention is based on the idea that eddy currents in the magnetic-reflux jacket can be tolerated if the electrical conductivity of the material is reduced and, thus, the strength of the eddy currents can be reduced as well. This is accomplished by a relatively high portion of chromium. Chromium, however, also has the benefit of increasing the resistance to corrosion. In a blood pump for intracorporeal use, this is of importance because blood is highly corrosive and, for reasons of space, the reflux will be in direct contact with blood. By using an unslotted shell, the magnetic losses of the magnetic reflux will be minimized as a result of an optimum utilization of the existing wall thickness (100% reflux). Thereby, the motor current needed for the required drive power is reduced.

The wall of the magnetic-reflux jacket preferably is uninterrupted or continuous and has a constant wall thickness. Only at the end of the shell, perforations can be provided which facilitate the anchoring to the plastic wall of the stator but will have no practical effects on the magnetic field since they are located outside the effective range of the magnetism. The material of the magnetic-reflux jacket is a metal alloy with crystalline structure. The material is softly magnetic so as to minimize the losses caused by hysteresis and respectively by magnetic reversal.

Preferably, the material of the magnetic-reflux jacket includes up to 8% aluminum. When such an alloy which includes aluminum is tempered at about 1100° C. in an oxygen-containing atmosphere, the aluminum will diffuse to the grain boundary of the iron crystals. Under the influence of oxygen, it will oxidize to $Al_2O_3$. Since aluminum oxide is a poor electric conductor, the iron crystals are insulated from each other. Thus, the insulated aluminum will effect a reduction of the eddy currents, so that a slotting or an axial layered configuration of the material of the magnetic-reflux jacket will not be required anymore. This effect also leads to an $Al_2O_3$ layer on the surface, thus resulting in an insulating and chemically inert layer for protection against blood.

Preferably, the material of the magnetic-reflux jacket includes up to 2% finely dispersed yttrium oxide. The yttrium oxide contributes to an increase of the specific resistance.

The above material should include no copper at all or merely a minimum of copper in order to keep the electric conductivity as low as possible.

A preferred alloy includes
iron as the main component
chromium up to 30%, preferably from 17% to 22%
aluminum up to 8%, preferably from 3% to 6%
yttrium oxide up to 2%
others up to 5%.

The percentages indicated above are always percent by weight.

An embodiment of the invention will be explained in greater detail hereunder with reference to the drawings.

In the drawings, the following is shown:

FIG. 1 is a side view of a pump with micromotor,

FIG. 2 is a longitudinal sectional view through FIG. 1, and

Figure 3:
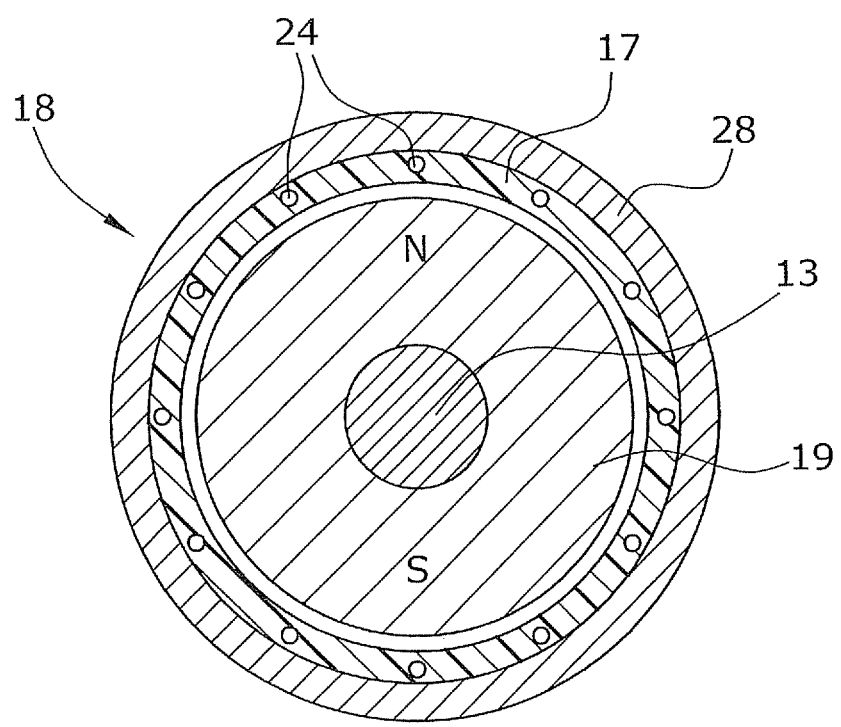
FIG. 3 is a cross-sectional view taken along III-III of FIG. 2.

The blood pump depicted in the Figures largely corresponds to the one according to WO 02/41935 A1. The pump comprises a micromotor 10 axially followed by a pump portion 11. Pump portion 11 includes an impeller 12 fastened to a shaft 13 and arranged for rotation within a tubular pump housing 14.

Micromotor 10 comprises a stator 15 and a rotor 16 connected to shaft 13. Stator 15 consists of a tubular shell 17 and a magnetic-reflux jacket 18 tightly surrounding said shell 17. Rotor 16 includes a magnet 19, with its north pole N and its south pole S arranged on diametrically opposite positions on the circumference. Magnet 19 is fastened to a shaft 13. Shaft 13 is supported on its rear end within shell 17 by means of a ball bearing 20 and, on its front end facing towards impeller 12, within a sealed bearing 21.

The rear end of stator 15 is followed by a transition portion 22 adapted for connecting of a catheter 25 to it. Wires 23 extend through transition piece 22 and connect to exciter coils 24 internally of the shell. Flowing through exciter coil 24 is an externally controlled alternating current whose frequency determines the rotational speed of the motor. The shell 17 accommodating the exciter coils 24 consists of a substantially 0.2 mm thick plastic layer with embedded wires. The wires are wound in two layers according to a predetermined configuration. Between stator 15 and rotor 16, a small gap exists, dimensioned in an order of magnitude of the tenth of a millimeter.

Magnetic-reflux jacket 18 consists of a one-pieced, tubular, unslotted shell. Simultaneously, it forms the outer skin of the micromotor. If required, it can also be covered by an additional plastic layer.

Magnetic-reflux jacket 18 tightly surrounds shell 17 containing the exciter coils 24.

The wall thickness of the magnetic-reflux jacket is about 0.25 mm, the outer diameter is 4 mm and the inner diameter is 3.45 mm. The length of magnetic-reflux jacket 18 is about 12 mm.

Back iron jacket 18 is axially continued in the form of webs 30 extending from the front end of the micromotor in the forward direction and integrally merging into the wall of pump housing 14. Thus, pump housing 14 is connected in one piece to magnetic-reflux jacket 18 by welding and thus can be made of a different weldable material. Therefore, the materials for the reflux of the motor and for the pump housing can each be optimally adapted to the individual requirements posed to them. This means that the pump housing 14 can have the same outer diameter as magnetic-reflux jacket 18 and a different inner diameter from that of magnetic-reflux jacket 18. In the present embodiment, the webs 30 are arranged parallel to the axis of the micromotor so that already as few as three webs will create a connection with sufficient stiffness against bending.

The openings 31 left between the webs 30 form the outlet opening of the pump, and the end-side opening 32 of pump housing 14 forms the inlet opening of the pump. The pump can also be driven in reverse direction so that said openings 31 form the inlet and said opening 32 forms the outlet.

According to a preferred embodiment, magnetic-reflux jacket 18 is made of a material distributed by Special Metals Corporation under the trademark INCOLOY MA956. This material contains the composition listed hereunder:

| | |
|---|---|
| iron | balance |
| chromium | 18.5%-21.5% |
| aluminum | 3.75%-5.75% |
| titanium | 0.2%-0.6% |
| carbon | 0.1% max. |
| yttrium oxide | 0.3%-0.7% |
| copper | 0.15% max. |
| manganese | 0.30% max. |
| cobalt | 0.3% max. |
| nickel | 0.50% max. |
| phosphorus | 0.02% max. |

From this material, there will first be produced a cylindrical shell which has the shape and size of the later magnetic-reflux jacket, and said shell will be preferably tempered for several hours at about 1100° C. while subjected to oxygen. In the process, the aluminum at the grain boundaries will partially oxidize to aluminum oxide and will distribute itself between the grain boundaries and along the surfaces of the shell. Thereafter, the shell surfaces will be provided with a thin insulating ceramic layer.

The shell formed by magnetic-reflux jacket 18 is formed with windows 33 on its proximal end. On the distal end, a welding seam 35 is arranged, connecting the magnetic-reflux jacket to pump housing 14.

Transition portion 22, which is made of plastic, is provided with integrally formed knobs 34 extending into the windows 33 and filling them in formlocking engagement. In this manner, there is achieved a stable connection to the catheter on the rear. Said windows 33 and the webs arranged therebetween are suitably located relative to the ball bearing 20 to the effect that a spreading of the magnetic field lines into the ball bearing is avoided. Also eddy currents in the bearing, which possibly could cause a reduction of the useful life, will be avoided in a corresponding manner.

In comparison to a magnetic-reflux jacket of the slotted type, the invention achieves an improvement of the magnetic properties of the magnetic-reflux jacket by introducing a larger quantity of iron material into the reflux. Thereby, the efficiency of the motor is improved. For a given desired hydraulic performance of the blood pump, the motor volume or the required motor current can be reduced.

A further advantage of the metal alloy resides in that the material of the magnetic-reflux jacket is weldable. This is beneficial in the assembly process for the motor.

The magnetic-reflux jacket has the following properties:
ferritic
high magnetic flux density
poor electric conductivity
corrosion resistance
weldability.

The invention claimed is:

1. A blood pump with micromotor sized for intravascular insertion, provided for intracorporeal use, said blood pump comprising:
a stator comprising:
a first shell;
an exciter coil embedded in the first shell and containing wires for conducting an alternating current; and
a magnetic-reflux jacket made of magnetically conductive material and fully surrounding the first shell, wherein the magnetic reflux jacket includes a one-piece unslotted second shell made of a ferritic alloy containing iron as the main component and up to 30% chromium, that reduces magnetic losses of magnetic reflux and the strength of eddy currents, thereby reducing the motor current for a required drive power of the blood pump compared to a magnetic-reflux jacket having a slotted shell.

2. The blood pump according to claim 1, wherein the ferritic alloy of the magnetic-reflux jacket contains up 3% to 8% aluminum.

3. The blood pump according to claim 1, wherein the ferritic alloy of the magnetic-reflux jacket contains up 0.3% to 2% yttrium oxide.

4. The blood pump according to claim 1, wherein the ferritic alloy of the magnetic-reflux jacket contains maximally 0.2% copper.

5. The blood pump according to claim 1, wherein the ferritic alloy of the magnetic-reflux jacket contains, apart from iron, the following components:

| | |
|---|---|
| chromium | 18.50%-21.50% |
| aluminum | 3.75%-5.75% |
| titanium | 0.20%-0.60% |
| carbon | 0.10% maximum |
| yttrium oxide | 0.30%-0.70% |
| copper | 0.15% maximum |
| manganese | 0.30% maximum |

-continued

| | |
|---|---|
| cobalt | 0.30% maximum |
| nickel | 0.50% maximum |
| phosphorus | 0.02% maximum. |

6. The blood pump according to claim 1, wherein the outer diameter of the magnetic-reflux jacket does not exceed 4.6 mm and the inner diameter is at least 3.3 mm.

7. The blood pump according to claim 1, wherein windows are provided on the proximal end of the magnetic-reflux jacket.

8. The blood pump according to claim 1, wherein the magnetic-reflux jacket is connected to a housing of the blood pump by a welding seam.

9. The blood pump according to claim 1, wherein the magnetic-reflux jacket is configured to reduce strength of eddy currents therein.

10. The blood pump according to claim 1, wherein the second shell is configured to reduce magnetic losses in the micromotor.

11. The blood pump according to claim 1, wherein the magnetic-reflux jacket comprises a constant wall thickness.

12. The blood pump according to claim 1, wherein the magnetic-reflux jacket is covered by a plastic layer.

13. The blood pump according to claim 1, further comprising a pump portion axially following the micromotor, wherein the pump portion comprises an impeller fastened to a shaft, and wherein the impeller is arranged for rotation within a pump housing.

* * * * *

UNITED STATES PATENT AND TRADEMARK OFFICE
CERTIFICATE OF CORRECTION

PATENT NO. : 10,808,704 B2
APPLICATION NO. : 12/532816
DATED : October 20, 2020
INVENTOR(S) : Thorsten Siess et al.

It is certified that error appears in the above-identified patent and that said Letters Patent is hereby corrected as shown below:

In the Specification

Column 2, Line 6 - Delete "performations" and insert --perforations-- therefor.

Signed and Sealed this
Twenty-seventh Day of September, 2022

Katherine Kelly Vidal
*Director of the United States Patent and Trademark Office*